(12) United States Patent
Steiger et al.

(10) Patent No.: US 8,546,594 B2
(45) Date of Patent: Oct. 1, 2013

(54) INDIUM OXOALKOXIDES FOR PRODUCING COATINGS CONTAINING INDIUM OXIDE

(75) Inventors: Juergen Steiger, Duesseldorf (DE); Duy Vu Pham, Oberhausen (DE); Heiko Thiem, Bensheim (DE); Alexey Merkulov, Ludwigshafen (DE); Arne Hoppe, Herne (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/809,322

(22) PCT Filed: Jul. 7, 2011

(86) PCT No.: PCT/EP2011/061493
§ 371 (c)(1),
(2), (4) Date: Jan. 9, 2013

(87) PCT Pub. No.: WO2012/010427
PCT Pub. Date: Jan. 26, 2012

(65) Prior Publication Data
US 2013/0116463 A1    May 9, 2013

(30) Foreign Application Priority Data
Jul. 21, 2010   (DE) .......................... 10 2010 031 592

(51) Int. Cl.
*C07F 5/00*   (2006.01)
(52) U.S. Cl.
USPC .......................................................... 556/1
(58) Field of Classification Search
USPC .......................................................... 556/1
See application file for complete search history.

(56) References Cited

U.S. PATENT DOCUMENTS

| 2004/0043630 | A1 | 3/2004 | Vaartstra et al. |
|---|---|---|---|
| 2005/0287819 | A1 | 12/2005 | Vaartstra et al. |
| 2011/0309313 | A1 | 12/2011 | Steiger et al. |
| 2011/0315982 | A1 | 12/2011 | Hoppe et al. |
| 2012/0181488 | A1 | 7/2012 | Steiger et al. |
| 2012/0202318 | A1 | 8/2012 | Steiger et al. |
| 2012/0289728 | A1 | 11/2012 | Steiger et al. |

FOREIGN PATENT DOCUMENTS

| WO | 2011 020781 | 2/2011 |
|---|---|---|
| WO | 2011 072887 | 6/2011 |
| WO | 2011 073005 | 6/2011 |
| WO | 2012 010427 | 1/2012 |
| WO | 2012 010464 | 1/2012 |
| WO | 2012 062575 | 5/2012 |

OTHER PUBLICATIONS

U.S. Appl. No. 13/516,900, filed Aug. 6, 2012, Steiger, et al.
U.S. Appl. No. 13/809,322, filed Jan. 9, 2013, Steiger, et al.

(Continued)

*Primary Examiner* — Porfirio Nazario Gonzalez
(74) *Attorney, Agent, or Firm* — Oblon, Spivak, McClelland, Maier & Neustadt, L.L.P.

(57) ABSTRACT

The present invention relates to halogenated indium oxo alkoxides of the generic formula $In_6O_2X_6(OR)_6(R'CH(O)COOR'')_2(HOR)_x(HNR'''_2)_y$ where X=F, Cl, Br and/or I, R=C1-C15-alkyl, C1-C15-alkenyl, C1-C15-alkynyl, C1-C15-alkoxyalkyl, C6-C15-aryl- and/or C7-C15-alkoxyaryl, R'=C1-C15-alkyl, C1-C15-alkenyl, C1-C15-alkynyl, C1-C15-alkoxyalkyl, C6-C15-aryl- and/or C7-C15-alkoxyaryl, R''=C1-C15-alkyl, C1-C15-alkenyl, C1-C15-alkynyl, C1-C15-alkoxyalkyl, C6-C15-aryl- and/or C7-C15-alkoxyaryl, R'''=C1-C15-alkyl, C1-C15-alkenyl, C1-C15-alkynyl, C1-C15-alkoxyalkyl, C6-C15-aryl- and/or C7-C15-alkoxyaryl, x=0 to 10 and y=0 to 10, to processes for preparation thereof and to use thereof.

20 Claims, 1 Drawing Sheet

Crystal structure of
$In_6O_2Cl_6(\mu_3\text{-}OCH_2CH_3)_6(\mu_2\text{-}CH_3CH(O)COOCH_2CH_3)_2(HOC_2H_5)_2(HN(CH_3)_2)_2$

(56) References Cited

OTHER PUBLICATIONS

U.S. Appl. No. 13/809,423, filed Jan. 10, 2013, Steiger, et al.

Kim, H., et al., "High Performance Solution-Processed Indium Oxide Thin-Film Transistors," J. Am. Chem. Soc., vol. 130, pp. 12580 to 12581, (2008) XP 002613079.

International Search Report Issued Oct. 11, 2011 in PCT/EP11/061493 Filed Jul. 7, 2011.

Crystal structure of
$In_6O_2Cl_6(\mu_2\text{-}OCH_2CH_3)_6(\mu_2\text{-}CH_3CH(O)COOCH_2CH_3)_2(HOC_2H_5)_2(HN(CH_3)_2)_2$
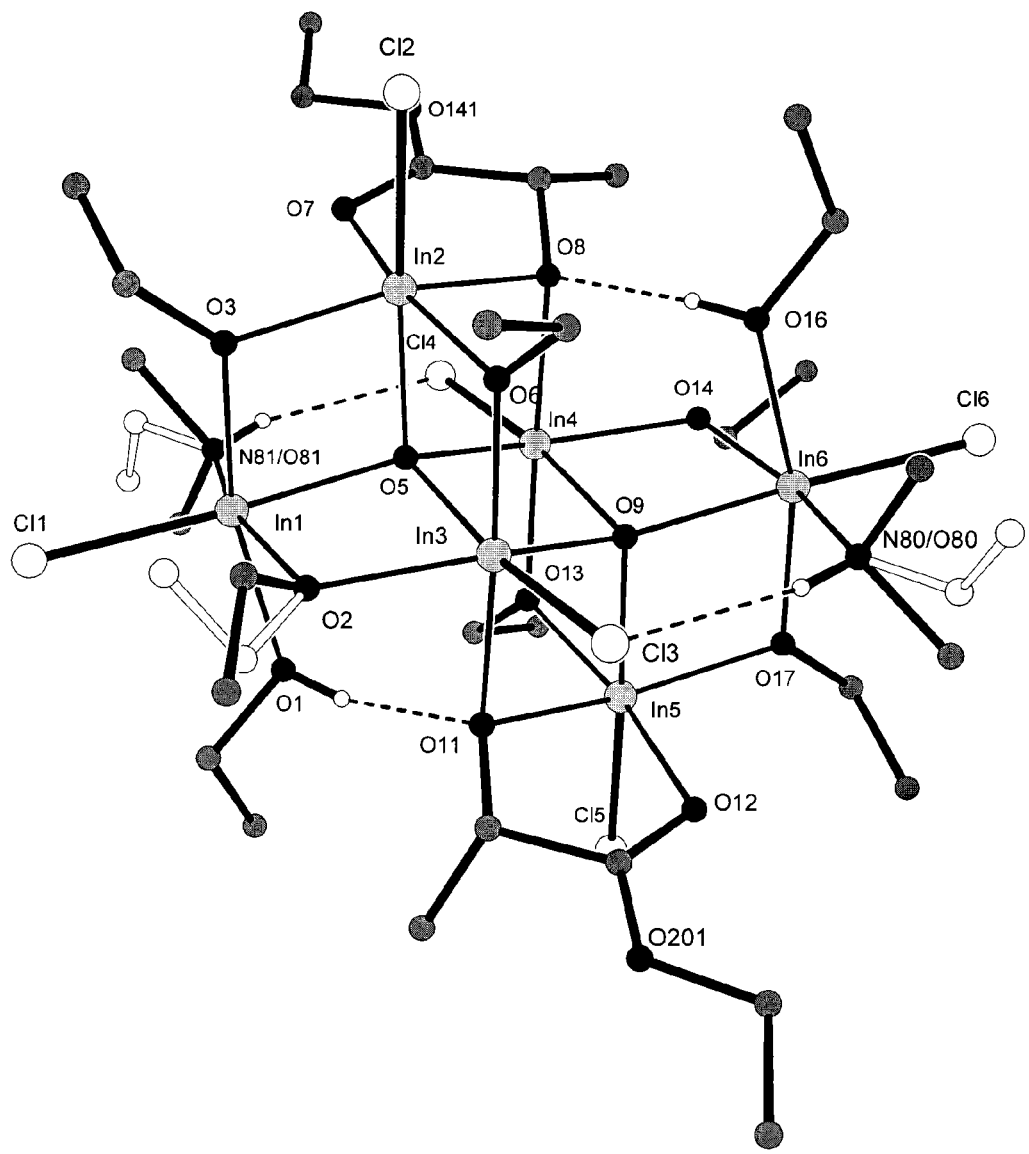

INDIUM OXOALKOXIDES FOR PRODUCING COATINGS CONTAINING INDIUM OXIDE

The present invention relates to indium oxo alkoxides for the production of indium oxide-containing layers, to processes for preparation thereof and to use thereof, especially for production of indium oxide-containing layers, as a constituent of coating compositions and for production of electronic components.

Indium oxide (indium(III) oxide, $In_2O_3$), owing to the large band gap between 3.6 and 3.75 eV (measured for vapour-deposited layers) [H. S. Kim, P. D. Byrne, A. Facchetti, T. J. Marks; *J. Am. Chem. Soc.* 2008, 130, 12580-12581], is a promising semiconductor. Thin films of a few hundred nanometers in thickness may additionally have a high transparency in the visible spectral range of greater than 90% at 550 nm. In extremely highly ordered single indium oxide crystals, it is additionally possible to measure charge carrier mobilities of up to 160 $cm^2/Vs$.

Indium oxide is often used in particular together with tin (IV) oxide ($SnO_2$) as the semiconductive mixed oxide ITO. Owing to the comparatively high conductivity of ITO layers with simultaneous transparency in the visible spectral range, one application thereof is in the field of liquid-crystal displays (LCDs), especially as a "transparent electrode". These usually doped metal oxide layers are produced industrially in particular by costly vapour deposition methods under high vacuum.

Indium oxide-containing layers and the production thereof, especially ITO layers and pure indium oxide layers, and the production thereof, are thus of great significance for the semiconductor and display industry.

Possible reactants and precursors discussed for the synthesis of indium oxide-containing layers include a multitude of compound classes. Examples include indium salts. For instance, Marks et al. describe components produced using a precursor solution composed of $InCl_3$ and the base monoethanolamine (MEA) dissolved in methoxyethanol. After spin-coating of the solution, the corresponding indium oxide layer is obtained by thermal treatment at 400° C. [H. S. Kim, P. D. Byrne, A. Facchetti, T. J. Marks; *J. Am. Chem. Soc.* 2008, 130, 12580-12581 and supplemental information].

Elsewhere, possible reactants or precursors discussed for the indium oxide synthesis are indium alkoxides. An indium alkoxide is a compound consisting of at least one indium atom, at least one alkoxide radical of the formula —OR (R=organic radical, especially R=alkyl radical) and optionally one or more organic radicals —R' (e.g. R'=alkyl radical, carboxyl radical, α-hydroxycarboxylic ester radical), one or more halogen radicals and/or one or more —OH or —OR'' radicals where R''=organic radical (especially R''=alkyl radical).

Independently of a possible use for indium oxide formation, the prior art describes various indium alkoxides and indium oxo alkoxides. Compared to the indium alkoxides already mentioned, indium oxo alkoxides also have at least one further oxygen radical (oxo radical) bound directly to an indium atom or bridging at least two indium atoms.

Mehrotra et al. describe the preparation of indium tris-alkoxide $In(OR)_3$ from indium(III) chloride ($InCl_3$) with Na—OR where R is methyl, ethyl, isopropyl, n-, s-, t-butyl and pentyl radicals. [S. Chatterjee, S. R. Bindal, R. C. Mehrotra; *J. Indian Chem. Soc.* 1976, 53, 867].

A review article by Carmalt et al. (Coordination Chemistry Reviews 250 (2006), 682-709) describes various gallium(III) and indium(III) alkoxides and aryloxides, some of which may also be present with bridging by means of alkoxide groups.

Additionally presented is an oxo-centred cluster of the formula $In_5(\mu\text{-}O)(O^iPr)_{13}$, more specifically $[In_5(\mu_5\text{-}O)(\mu_3O^iPr)_4(\mu_2\text{-}O^iPr)_4(O^iPr)_5]$, which is an oxo alkoxide and cannot be prepared from $[In(O^iPr)_3]$.

A review article by N. Turova et al., Russian Chemical Reviews 73 (11), 1041-1064 (2004) summarizes synthesis, properties and structures of metal oxo alkoxides, which are considered therein as precursors for the production of oxidic materials via sol-gel technology. In addition to a multitude of other compounds, the synthesis and structure of $[Sn_3O(O^iBu)_{10}(^tBuOH)_2]$, of the already mentioned compound $[In_5O(O^iPr)_{13}]$ and of $[Sn_6O_4(OR)_4]$ (R=Me, $Pr^i$) are described.

The article by N. Turova et al., Journal of Sol-Gel Science and Technology, 2, 17-23 (1994) presents results of studies on alkoxides, which are considered therein as a scientific basis for the development of sol-gel processes of alkoxides and alkoxide-based powders. In this context, there is also discussion of a purported "indium isopropoxide", which was found to be the oxo alkoxide with a central oxygen atom and five surrounding metal atoms of the formula $M_5(\mu\text{-}O)(O^iPr)_{13}$ which is also described in Carmalt et al.

A synthesis of this compound and the crystal structure thereof are described by Bradley et al., J. Chem. Soc., Chem. Commun., 1988, 1258-1259. Further studies by the authors led to the result that the formation of this compound cannot be attributed to a hydrolysis of intermediately formed $In(O^iPr)_3$ (Bradley et al., Polyhedron Vol. 9, No. 5, pp. 719-726, 1990). Suh et al., J. Am. Chem. Soc. 2000, 122, 9396-9404 additionally found that this compound is not preparable by a thermal route either from $In(O^iPr)_3$. Moreover, Bradley (Bradley et al., Polyhedron Vol. 9, No. 5, pp. 719-726, 1990) found that this compound cannot be sublimed.

Metal oxide layers can in principle be produced via various processes.

One means of producing metal oxide layers is based on sputtering techniques. However, these techniques have the disadvantage that they have to be performed under high vacuum. A further disadvantage is that the films produced therewith have many oxygen defects, which make it impossible to establish a controlled and reproducible stoichiometry of the layers and hence lead to poor properties of the layers produced.

Another means in principle for producing metal oxide layers is based on chemical gas phase deposition. For example, it is possible to produce indium oxide-containing layers from indium oxide precursors such as indium alkoxides or indium oxo alkoxides via gas phase deposition. For example U.S. Pat. No. 6,958,300 B2 teaches using at least one metal organo oxide precursor (alkoxide or oxo alkoxide) of the generic formula $M^1_q(O)_x(OR^1)_y$ (q=1-2; x=0-4, y=1-8, $M^1$=metal; e.g. Ga, In or Zn, $R^1$=organic radical; alkoxide when x=0, oxo alkoxide when ≥1) in the production of semiconductors or metal oxide layers by gas phase deposition, for example CVD or ALD. However, all gas phase deposition processes have the disadvantage that they require either i) in the case of a thermal reaction regime, the use of very high temperatures, or ii) in the case of introduction of the required energy for the decomposition of the precursor in the form of electromagnetic radiation, high energy densities. In both cases, it is possible only with a very high level of apparatus complexity to introduce the energy required to decompose the precursor in a controlled and homogeneous manner.

Advantageously, metal oxide layers are thus produced by means of liquid phase processes, i.e. by means of processes comprising at least one process step before the conversion to the metal oxide, in which the substrate to be coated is coated with a liquid solution of at least one precursor of the metal oxide, optionally dried subsequently, and converted. A metal oxide precursor is understood to mean a compound decomposable thermally or with electromagnetic radiation, with which metal oxide-containing layers can be formed in the presence or absence of oxygen or other oxidizing substances. Prominent examples of metal oxide precursors are, for example, metal alkoxides. In principle, the layer can be produced i) by sol-gel processes in which the metal alkoxides used are converted first to gels in the presence of water by hydrolysis and subsequent condensation, and then to metal oxides, or ii) from nonaqueous solution.

The production of indium oxide-containing layers from indium alkoxides from the liquid phase also forms part of the prior art.

The production of indium oxide-containing layers from indium alkoxides via sol-gel processes in the presence of significant amounts of water forms part of the prior art. WO 2008/083310 A1 describes processes for producing inorganic layers or organic/inorganic hybrid layers on a substrate, in which a metal alkoxide (for example one of the generic formula $R^1M\text{-}(OR^2)_{y\text{-}x}$) or a prepolymer thereof is applied to a substrate, and then the resulting metal alkoxide layer is hardened in the presence of, and reacting with, water. The metal alkoxides usable may include those of indium, gallium, tin or zinc. However, a disadvantage of the use of sol-gel processes is that the hydrolysis-condensation reaction is started automatically by addition of water and is controllable only with difficulty after it has started. When the hydrolysis-condensation process is started actually before the application to the substrate, the gels obtained in the meantime, owing to their elevated viscosity, are often unsuitable for processes for obtaining fine oxide layers. When the hydrolysis-condensation process, in contrast, is started only after application to the substrate by supply of water in liquid form or as a vapour, the resulting poorly mixed and inhomogeneous gels often lead to correspondingly inhomogeneous layers with disadvantageous properties.

JP 2007-042689 A describes metal alkoxide solutions which may contain indium alkoxides, and also processes for producing semiconductor components which use these metal alkoxide solutions. The metal alkoxide films are treated thermally and converted to the oxide layer; these systems too, however, do not afford sufficiently homogeneous films. Pure indium oxide layers, however, cannot be produced by the process described therein.

DE 10 2009 009 338, which was yet to be published at the priority date of the present application, describes the use of indium alkoxides in the production of indium oxide-containing layers from anhydrous solutions. Although the resulting layers are more homogeneous than layers produced by means of sol-gel processes, the use of indium alkoxides in anhydrous systems still has the disadvantage that the conversion of indium alkoxide-containing formulations to indium oxide-containing layers does not give sufficiently good electrical performance of the resulting layer.

DE 10 2009 028 801, which was likewise yet to be published at the priority date of the present application, describes a liquid phase process for producing comparatively improved indium oxide-containing layers from nonaqueous solution, in which an anhydrous composition containing i) at least one indium oxo alkoxide of the generic formula $M_xO_y(OR)_z[O(R'O)_cH]_a X_b[R''OH]_d$ where M=In, x=3-25, y=1-10, z=3-50, a=0-25, b=0-20, c=0-1, d=0-25, R, R', R''=organic radical, X=F, Cl, Br, I and ii) at least one solvent is applied to a substrate, optionally dried, and converted to an indium oxide-containing layer.

DE 10 2009 054 997, which was yet to be published at the priority date of the present application, additionally describes a process for production of indium oxide-containing layers from solution, in which an anhydrous composition containing at least one indium halogen alkoxide of the generic formula $InX(OR)_2$ where R=alkyl radical and/or alkoxyalkyl radical and X=F, Cl, Br or I, and at least one solvent or dispersion medium is applied to a substrate, the composition applied to the substrate is irradiated with electromagnetic radiation of wavelength 360 nm, optionally dried, and then converted thermally to an indium oxide-containing layer.

Nevertheless, the production of even better indium oxide-containing layers is desirable. It is thus an object of the present invention to provide substances which can be used for production of indium oxide-containing layers (especially of indium oxide layers) with even better electrical performance (especially even better field-effect mobilities $\mu_{FET}$). It would also be desirable to provide substances which can be processed in a simpler manner.

This object is achieved in the present document by the inventive halogenated indium oxo alkoxide of the generic formula $In_6O_2X_6(OR)_6(R'CH(O)COOR'')_2(HOR)_x(HNR'''_2)_y$ where X=F, Cl, Br and/or I, R=C1-C15-alkyl, C1-C15-alkenyl, C1-C15-alkynyl, C1-C15-alkoxyalkyl, C6-C15-aryl- and/or C7-C15-alkoxyaryl, R'=C1-C15-alkyl, C1-C15-alkenyl, C1-C15-alkynyl, C1-C15-alkoxyalkyl, C6-C15-aryl- and/or C7-C15-alkoxyaryl, R''=C1-C15-alkyl, C1-C15-alkenyl, C1-C15-alkynyl, C1-C15-alkoxyalkyl, C6-C15-aryl- and/or C7-C15-alkoxyaryl, R'''=C1-C15-alkyl, C1-C15-alkenyl, C1-C15-alkynyl, C1-C15-alkoxyalkyl, C6-C15-aryl- and/or C7-C15-alkoxyaryl, x=0 to 10 and y=0 to 10. Surprisingly, it is additionally possible with these substances to produce particularly high-quality indium oxide-containing layers under air. The inventive compounds are halogenated indium oxo alkoxides which, in addition to the oxo and alkoxide radicals already mentioned, are additionally coordinated by ligands based on α-hydroxy esters and optionally by alcohols and/or secondary amines.

These compounds $In_6O_2X_6(OR)_6(R'CH(O)COOR'')_2(HOR)_x(HNR'''_2)_y$, which have not been described to date in the literature, can be prepared via a reaction of indium(III) halogen alkoxide adducts or indium(III) oxo halogen alkoxide adducts, preferably indium(III) halogen dialkoxides of the generic formula $InX(OR)_2(HNR'''_2)_y$ where X=F, Cl, Br, I and R=C1-C15-alkyl, C1-C15-alkenyl, C1-C15-alkynyl, C1-C15-alkoxyalkyl, C6-C15-aryl- and/or C7-C15-alkoxyaryl, R'''=C1-C15-alkyl, C1-C15-alkenyl, C1-C15-alkynyl, C1-C15-alkoxyalkyl, C6-C15-aryl- and/or C7-C15-alkoxyaryl and y=0-10 (preparable by reaction of compositions comprising an indium trihalide $InX_3$ where X=F, Cl, Br and/or I and at least one alcohol of the generic formula ROH where R=C1-C15-alkyl, C1-C15-alkenyl, C1-C15-alkynyl, C1-C15-alkoxyalkyl, C6-C15-aryl- and/or C7-C15-alkoxyaryl with at least one secondary amine of the generic formula $R'''_2NH$ where R'''=C1-C15-alkyl, C1-C15-alkenyl, C1-C15-alkynyl, C1-C15-alkoxyalkyl, C6-C15-aryl- and/or C7-C15-alkoxyaryl, cf. also DE 10 2009 054 998 (which was yet to be published at the priority date of the present application)) with the appropriate α-hydroxy esters in preferably alcoholic solution.

Preferred indium oxo alkoxides are the corresponding chlorides, i.e. corresponding compounds in which X=Cl. These compounds lead to particularly good electrical properties of the corresponding indium oxide-containing layer and can be prepared in a particularly simple manner.

Preference is likewise given to corresponding indium oxo alkoxides in which R=—CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$) or —C(CH$_3$)$_3$ and which are preparable and processible in a particularly simple manner.

Preference is additionally given to corresponding indium oxo alkoxides in which R=—CH$_2$CH$_2$—OCH$_3$, —CH$_2$CH$_2$—OCH$_2$CH$_3$, —CH$_2$CH$_2$—OCH$_2$CH$_2$CH$_3$, —CH$_2$CH$_2$—OCH(CH$_3$)$_2$, —CH$_2$CH$_2$—OCH$_2$CH$_2$CH$_2$CH$_3$, —CH$_2$CH$_2$—OCH$_2$CH(CH$_3$)$_2$, —CH$_2$CH$_2$—OCH(CH$_3$)(CH$_2$CH$_3$) or —CH$_2$CH$_2$—OC(CH$_3$)$_3$ and which are preparable and processible in a particularly simple manner.

Preferred R' radicals are R'=—CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$) or —C(CH$_3$)$_3$. The corresponding compounds are also preparable in a particularly simple manner and lead to particularly good layers.

Preferred R" radicals are R"=—CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$) or —C(CH$_3$)$_3$. The corresponding compounds are likewise preparable in a particularly simple manner and lead to particularly good layers.

In addition, preferred R'" radicals=—CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$) or —C(CH$_3$)$_3$. The corresponding compounds are equally preparable in a particularly simple manner and lead to particularly good layers.

Since the inventive indium oxo alkoxides belong to the class of the coordinated compounds, it is possible to replace the noncovalently bonded ligands (amine and alcohol) by the ligand exchange or the change in the reaction conditions. Particular preference is therefore given to indium oxo alkoxides where x=0 to 5 and y=0 to 5. Very particular preference is given to indium oxo alkoxides where x=1 to 3 and y=1 to 3. The corresponding compounds are likewise preparable in a particularly simple manner and lead to particularly good layers.

A particularly preferred inventive indium oxo alkoxide is an indium oxo alkoxide of the generic formula In$_6$O$_2$Cl$_6$(OCH$_2$CH$_3$)$_6$(CH$_3$CH(O)COOCH$_2$CH$_3$)$_2$(HN(CH$_3$)$_2$)$_2$ which may have the structural formula shown in FIG. 1 and which may additionally be present with up to 10 ethanol and/or amine molecules coordinated in the crystal.

The present invention further provides a process for preparing the inventive indium oxo alkoxides, in which an indium(III) salt of the formula InX$_3$ where X=F, Cl, Br and/or I is converted first in the presence of an alcohol ROH where R=C1-C15-alkyl, C1-C15-alkenyl, C1-C15-alkynyl, C1-C15-alkoxyalkyl, C6-C15-aryl- and/or C7-C15-alkoxyaryl and in the presence of a secondary amine of the generic formula HNR'"$_2$ where R'"=C1-C15-alkyl, C1-C15-alkenyl, C1-C15-alkynyl, C1-C15-alkoxyalkyl, C6-C15-aryl- and/or C7-C15-alkoxyaryl to give an indium(III) halogen alkoxide adduct or indium(III) oxo halogen alkoxide adduct, which is subsequently reacted with at least one α-hydroxy ester R'CH(OH)COOR" where R'=C1-C15-alkyl, C1-C15-alkenyl, C1-C15-alkynyl, C1-C15-alkoxyalkyl, C6-C15-aryl- and/or C7-C15-alkoxyaryl and R"=C1-C15-alkyl, C1-C15-alkenyl, C1-C15-alkynyl, C1-C15-alkoxyalkyl, C6-C15-aryl- and/or C7-C15-alkoxyaryl (preferably in alcoholic solution).

In the process according to the invention, the molar ratio of amine used (NHR'"$_2$) to indium(III) salt is preferably >2.5:1, especially 4 to 10:1. The alcohol (ROH) used is simultaneously the solvent. The molar ratio of alcohol (ROH) used to the indium(III) salt used is preferably >2.5:1, more preferably 10 to 100:1.

An indium(III) salt preferred for the process is the corresponding chloride. Proceeding from the corresponding chloride, it is possible to arrive at compounds which lead to indium oxide-containing layers with particularly good electrical properties and can additionally be prepared in a particularly simple manner.

Preference is likewise given to corresponding alcohols in which R=—CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$) or —C(CH$_3$)$_3$ and which are preparable and processible in a particularly simple manner.

Preference is additionally given to corresponding alkoxy alcohols in which R=—CH$_2$CH$_2$—OCH$_3$, —CH$_2$CH$_2$—OCH$_2$CH$_3$, —CH$_2$CH$_2$—OCH$_2$CH$_2$CH$_3$, —CH$_2$CH$_2$—OCH(CH$_3$)$_2$, —CH$_2$CH$_2$—OCH$_2$CH$_2$CH$_2$CH$_3$, —CH$_2$CH$_2$—OCH$_2$CH(CH$_3$)$_2$, —CH$_2$CH$_2$—OCH(CH$_3$)(CH$_2$CH$_3$) or —CH$_2$CH$_2$—OC(CH$_3$)$_3$ and which are preparable and processible in a particularly simple manner.

In addition, preferred amine radicals R'"=—CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$) or —C(CH$_3$)$_3$. The corresponding compounds are likewise preparable in a particularly simple manner and lead to particularly good layers.

Preferably, the intermediate formed from the indium(III) salt is an indium(III) halogen dialkoxide of the generic formula InX(OR)$_2$(HNR'"$_2$)$_y$ where X=F, Cl, Br, or I, R=C1-C15-alkyl, C1-C15-alkenyl, C1-C15-alkynyl, C1-C15-alkoxyalkyl, C6-C15-aryl- and/or C7-C15-alkoxyaryl, R'"=C1-C15-alkyl, C1-C15-alkenyl, C1-C15-alkynyl, C1-C15-alkoxyalkyl, C6-C15-aryl- and/or C7-C15-alkoxyaryl and y=0 to 10, which is subsequently reacted with the at least one α-hydroxy ester R'CH(OH)COOR" where R'=C1-C15-alkyl, C1-C15-alkenyl, C1-C15-alkynyl, C1-C15-alkoxyalkyl, C6-C15-aryl- and/or C7-C15-alkoxyaryl and R"=C1-C15-alkyl, C1-C15-alkenyl, C1-C15-alkynyl, C1-C15-alkoxyalkyl, C6-C15-aryl- and/or C7-C15-alkoxyaryl (preferably in alcoholic solution).

In the process according to the invention, the molar ratio of α-hydroxy ester R'CH(OH)COOR" used to indium(III) salt is preferably >0.33:1, especially 0.34 to 5:1.

Particularly good yields result in the process according to the invention when the process described is performed with an indium(III) halogen alkoxide adduct selected from the group of compounds InCl(OCH$_3$)$_2$(HNMe$_2$)$_2$, InCl(OCH$_2$CH$_3$)$_2$(HNMe$_2$)$_2$, InCl(OCH$_2$CH$_2$CH$_3$)$_2$(HNMe$_2$)$_2$, InCl(OCH(CH$_3$)$_2$)$_2$(HNMe$_2$)$_2$, InCl(OCH$_2$CH$_2$CH$_2$CH$_3$)$_2$(HNMe$_2$)$_2$, InCl(OCH(CH$_3$)(CH$_2$CH$_3$))$_2$(HNMe$_2$)$_2$, and InCl(OC(CH$_3$)$_3$)$_2$(HNMe$_2$)$_2$. Correspondingly preferred process products are compounds of the In$_6$O$_2$Cl$_6$(OR)$_6$(R'CH(O)COOR")$_2$(HOR)$_x$(HNMe$_2$)$_y$ type where R=—OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH(CH$_3$)(CH$_2$CH$_3$) or —OC(CH$_3$)$_3$.

Preferred α-hydroxy ester radicals R' are R'=—CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$) or —C(CH$_3$)$_3$. The corresponding compounds are also preparable in a particularly simple manner and lead to particularly good layers.

Preferred R" radicals are R"=—CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$) or —C(CH$_3$)$_3$.

The corresponding compounds are likewise preparable in a particularly simple manner and lead to particularly good layers.

In addition, particularly good yields and precursors suitable for particularly high-value semiconductor layers result when the α-hydroxy ester used is selected from the group consisting of methyl lactate, ethyl lactate, n-propyl lactate and n-butyl lactate. The products formed contain the corresponding alkyl lactates as ligands.

The reaction is further preferably performed in aprotic or alcoholic solution. In the case of the preferred use of alcoholic solutions, however, the alcohol should be selected to achieve a homogeneous product such that it corresponds to the alkoxide radical OR of the indium(III) halogen dialkoxide used. Very particular preference is given to performing the reaction in an alcohol selected from the group consisting of $HOCH_3$, $HOCH_2CH_3$, $HOCH_2CH_2CH_3$, $HOCH(CH_3)_2$, $HOCH_2CH_2CH_2CH_3$, $HOCH(CH_3)(CH_2CH_3)$, $HOCH_2CH(CH_3)_2$ or $HOC(CH_3)_3$.

With the process according to the invention it is possible in a particularly efficient manner to produce the indium oxo alkoxides of the generic formula
$$In_6O_2X_6(\mu_2\text{-}OR)_6(\mu_2\text{-}R'OH(O)COOR'')_2(HOR)_x(HNR''')_y,$$
which are preferred for that reason, and the very particularly preferred indium oxo alkoxide of the formula
$$In_6O_2Cl_6(\mu_2\text{-}OCH_2CH_3)_6(\mu_2\text{-}CH_3CH(O)COOCH_2CH_3)_2(HOC_2H_5)_2(HN(CH_3)_2)_2.$$
This compound can be prepared as described in the appended example.

The present invention further provides for the use of the inventive indium oxo alkoxides for production of indium oxide-containing layers, and corresponding processes for producing indium oxide-containing layers. The inventive indium oxo alkoxide is suitable in principle for layer production via sputtering processes, via gas phase deposition, for sol-gel processes and for deposition from aqueous and nonaqueous solution.

The process product of the process according to the invention, the indium oxide-containing layer, is understood to mean a metal- or semimetal-containing layer which comprises indium atoms or ions present essentially in oxidic form. Optionally, the indium oxide-containing layer may also comprise carbon, nitrogen, halogen or alkoxide components from an incomplete conversion or an incomplete removal of by-products formed. The indium oxide-containing layer may be a pure indium oxide layer, i.e. neglecting any carbon, nitrogen, alkoxide or halogen components may consist essentially of indium atoms or ions present in oxidic form, or comprise proportions of further elements which may themselves be present in elemental, oxidic or another form. To obtain pure indium oxide layers, only indium-containing precursors should be used in the process according to the invention, preferably only indium oxo alkoxides and indium alkoxides in addition to the inventive at least one indium oxo alkoxide. In contrast, to obtain layers comprising other metals in addition to the indium-containing precursors, it is also possible to use precursors of metals in the 0 oxidation state (to prepare layers containing further metals in uncharged form) or metal oxide precursors (for example other metal alkoxides or oxo alkoxides).

The present process according to the invention is particularly suitable for producing indium oxide layers when the inventive indium oxo alkoxide is used as the sole metal oxide precursor. Very particularly good layers result when the sole metal oxide precursor corresponds to the formula $In_6O_2Cl_6(OCH_2CH_3)_6(CH_3CH(O)COOCH_2CH_3)_2(HOC_2H_5)_2(HN(CH_3)_2)$.

For layer production, the indium oxo alkoxide is preferably used in aqueous or nonaqueous coating compositions. In these, the at least one indium oxo alkoxide is preferably present in proportions of 0.1 to 15% by weight, more preferably 1 to 10% by weight, most preferably 2 to 5% by weight, based on the total mass of the composition.

The composition may further contain preferably at least one solvent, i.e. the composition may contain either one solvent or a mixture of different solvents. Usable with preference in the formulation for the process according to the invention are aprotic and weakly protic solvents, i.e. those selected from the group of the aprotic nonpolar solvents, i.e. of the alkanes, substituted alkanes, alkenes, alkynes, aromatics without or with aliphatic or aromatic substituents, halogenated hydrocarbons, tetramethylsilane, the group of the aprotic polar solvents, i.e. of the ethers, aromatic ethers, substituted ethers, esters or acid anhydrides, ketones, tertiary amines, nitromethane, DMF (dimethylformamide), DMSO (dimethylsulphoxide) or propylene carbonate, and the weakly protic solvents, i.e. the alcohols, the primary and secondary amines and formamide. Solvents usable with particular preference are alcohols, and also toluene, xylene, anisole, mesitylene, n-hexane, n-heptane, tris(3,6-dioxaheptyl)amine (TDA), 2-aminomethyltetrahydrofuran, phenetole, 4-methylanisole, 3-methylanisole, methyl benzoate, ethyl benzoate, ethyl lactate, butyl acetate, N-methyl-2-pyrrolidone (NMP), tetralin and diethyl ether. Very particularly preferred solvents are methanol, ethanol, isopropanol, tetrahydrofurfuryl alcohol, tert-butanol, n-butanol, ethyl lactate, butyl acetate and toluene, and mixtures thereof.

To achieve particularly good printability, the composition used in the process according to the invention preferably has a viscosity of 1 mPa·s to 10 Pa·s, especially 1 mPa·s to 100 mPa·s, determined to DIN 53019 parts 1 to 2 and measured at 20° C. Corresponding viscosities can be established by adding polymers, cellulose derivatives, or $SiO_2$ obtainable, for example, under the Aerosil trade name, and especially by means of PMMA, polyvinyl alcohol, urethane thickeners or polyacrylate thickeners.

The substrate which is used in the process according to the invention is preferably a substrate consisting of glass, silicon, silicon dioxide, a metal oxide or transition metal oxide, a metal or a polymeric material, especially PI or PET.

Indium oxide-containing layers are preferably produced by means of a coating process selected from printing processes (especially flexographic/gravure printing, inkjet printing, offset printing, digital offset printing and screen printing), spraying processes, rotary coating processes ("spin-coating"), dipping processes ("dip-coating"), and processes selected from meniscus coating, slit coating, slot-die coating and curtain coating. The coating process is most preferably a printing process.

After the coating and before the conversion, the coated substrate can additionally be dried. Corresponding measures and conditions for this purpose are known to those skilled in the art.

The conversion to an indium oxide-containing layer can be effected by a thermal route and/or by irradiation with electromagnetic, especially actinic, radiation. Preference is given to converting by a thermal route by means of temperatures of greater than 150° C. Particularly good results can be achieved, however, when temperatures of 250° C. to 360° C. are used for conversion.

Typically, conversion times of a few seconds up to several hours are used.

The thermal conversion can additionally be promoted by injecting UV, IR or VIS radiation or treating the coated substrate with air or oxygen before, during or after the thermal treatment.

The quality of the layer obtained by the process according to the invention can additionally be improved further by a combined thermal and gas treatment (with $H_2$ or $O_2$), plasma treatment (Ar, $N_2$, $O_2$ or $H_2$ plasma), laser treatment (with wavelengths in the UV, VIS or IR range) or an ozone treatment, which follows the conversion step.

The invention further provides indium oxide-containing layers producible by means of the inventive indium oxo alkoxides. Indium oxide-containing layers which are producible from the inventive indium oxo alkoxides and are pure indium oxide layers have particularly good properties.

Owing to the good suitability of the inventive indium oxo alkoxides for the production of indium oxide-containing layers from the liquid phase, the present invention further provides for the use of the inventive indium oxo alkoxides for production of liquid coating compositions. Liquid coating compositions are understood to mean those which are in liquid form under SATP conditions ("Standard Ambient Temperature and Pressure"; T=25° C. and p=1013 hPa) and on application to the substrate to be coated.

The inventive indium oxo alkoxides are additionally advantageously suitable for the production of electronic components, especially the production of transistors (especially thin-layer transistors), displays, RFID tags, circuits, diodes, sensors or solar cells.

The examples which follow are intended to illustrate the subject-matter of the present invention in detail without restriction.

WORKING EXAMPLES

1a) Synthesis of an Indium(III) Halogen Alkoxide or Indium(III) Oxo Halogen Alkoxide for Use (Intermediate)

In a 500 ml glass round-bottom flask which has been freed of residual moisture, 5.0 g of indium(III) chloride ($InCl_3$, 22.5 mmol) are dissolved in 250 ml of dried methanol by stirring under protective gas atmosphere, which leaves a residue of $InCl_3$ of <10% by weight (based on the starting weight). The metered addition of the dimethylamine base (5.0 g corresponding to 111 mmol) is controlled by means of a mass flow controller and it is added over a period of five hours. Subsequently, the solution is evaporated fully, and the remaining solid is taken up with 250 ml of dried methanol, filtered under $N_2$ protective gas, washed repeatedly with dried methanol and dried at room temperature under reduced pressure (<10 mbar) for 12 h. The product yield was >80 mol %.

1b) Synthesis of $In_6(O)_2(\mu_2\text{-}OC_2H_5)_6(\mu_2\text{-}CH_3CH(O)COOC_2H_5)_2(Cl)_6(HOC_2H_5)_2(HN(CH_3)_2)_2$ In a 250 ml glass round-bottom flask which has been freed of residual moisture, 5.0 g of the product obtained according to 1a) were dissolved in 100 ml of ethanol under protective gas atmosphere. The slightly turbid solution which formed was filtered, and 5 ml of ethyl lactate were added. After stirring at room temperature for 1 h, 5 ml of butyl acetate were added for the crystal formation. After two days, crystals formed were isolated and analyzed. The product is $In_6(O)_2(\mu_2\text{-}OC_2H_5)_6(\mu_2\text{-}CH_3CH(O)COOC_2H_5)_2(Cl)_6(HOC_2H_5)_2(HN(CH_3)_2)_2$, which has the crystal structure shown in FIG. 1.

1c) Production of Indium Oxide Layers

A doped silicon substrate with an edge length of about 15 mm and with a silicon oxide coating of thickness approx. 200 nm and finger structures of ITO/gold was coated with 100 μl of a 5% by weight solution containing the product formed in 1b) in ethanol by spin-coating (2000 rpm). After the coating operation, the coated substrate was heat treated under air at a temperature of 260° C. or 350° C. for one hour.

The inventive coating shows (cf. table 1) a charge carrier mobility of up to 2 $cm^2/Vs$ (at gate-source voltage 30 V, source-drain voltage 30 V, channel width 0.2 cm and channel length 20 μm).

TABLE 1

| Charge carrier mobilities | | |
|---|---|---|
| | Charge carrier mobility/$cm^2V^{-1}s^{-1}$ | |
| Solvents | 260° C. | 350° C. |
| Ethanol | 0.3 | 2.0 |

The invention claimed is:

1. An indium oxo alkoxide of formula:

$$In_6O_2X_6(OR)_6(R'CH(O)COOR'')_2(HOR)_x(HNR'''_2)_y,$$

wherein X is at least one selected from the group consisting of F, Cl, Br and I;
R is at least one selected from the group consisting of C1-C15-alkyl, C1-C15-alkenyl, C1-C15-alkynyl, C1-C15-alkoxyalkyl, C6-C15-aryl- and C7-C15-alkoxyaryl;
R' is at least one selected from the group consisting of C1-C15-alkyl, C1-C15-alkenyl, C1-C15-alkynyl, C1-C15-alkoxyalkyl, C6-C15-aryl- and C7-C15-alkoxyaryl;
R" is at least one selected from the group consisting of C1-C15-alkyl, C1-C15-alkenyl, C1-C15-alkynyl, C1-C15-alkoxyalkyl, C6-C15-aryl- and C7-C15-alkoxyaryl;
R''' is at least one selected from the group consisting of C1-C15-alkyl, C1-C15-alkenyl, C1-C15-alkynyl, C1-C15-alkoxyalkyl, C6-C15-aryl- and C7-C15-alkoxyaryl;
x is of from 0 to 10; and
y is of from 0 to 10.

2. The indium oxo alkoxide of claim 1, having formula:

$$In_6O_2Cl_6(OCH_2CH_3)_6(CH_3CH(O)COOCH_2CH_3)_2(HN(CH_3)_2)_2.$$

3. A process for preparing the indium oxo alkoxide of claim 1, comprising
converting an indium(III) salt of formula $InX_3$
first in presence of an alcohol ROH
and in presence of a secondary amine of formula $HNR'''_2$
to obtain an indium(III) halogen alkoxide adduct or an indium(III) oxo halogen alkoxide adduct, and
reacting the indium(III) halogen alkoxide adduct or the indium(III) oxo halogen alkoxide adduct with at least one α-hydroxy ester R'CH(OH)COOR".

4. The process of claim 3,
wherein the indium(III) halogen alkoxide adduct formed as an intermediate is of formula $InX(OR)_2(HNR'''_2)_y$,
wherein X=F, Cl, Br, or I;

R is at least one selected from the group consisting of C1-C15-alkyl, C1-C15-alkenyl, C1-C15-alkynyl, C1-C15-alkoxyalkyl, C6-C15-aryl- and C7-C15-alkoxyaryl;

R''' is at least one selected from the group consisting of C1-C15-alkyl, C1-C15-alkenyl, C1-C15-alkynyl, C1-C15-alkoxyalkyl, C6-C15-aryl- and C7-C15-alkoxyaryl; and y is of from 0 to 10.

5. The process of claim 4, wherein the indium(III) halogen alkoxide adduct is at least one selected from the group consisting of $InCl(OCH_3)_2(HNMe_2)_2$, $InCl(OCH_2CH_3)_2(HNMe_2)_2$, $InCl(OCH_2CH_2CH_3)_2(HNMe_2)_2$, $InCl(OCH(CH_3)_2)_2(HNMe_2)_2$, $InCl(OCH_2CH_2CH_2CH_3)_2(HNMe_2)_2$, $InCl(OCH(CH_3)(CH_2CH_3))_2(HNMe_2)_2$, and $InCl(OC(CH_3)_3)_2(HNMe_2)_2$.

6. The process of claim 3, wherein the a-hydroxy ester is at least one selected from the group consisting of methyl lactate, ethyl lactate, n-propyl lactate, and n-butyl lactate.

7. The process of claim 3, wherein the process is performed in a solution comprising an alcohol, and the alcohol is at least one selected from the group consisting of $HOCH_3$, $HOCH_2CH_3$, $HOCH_2CH_2CH_3$, $HOCH(CH_3)_2$, $HOCH_2CH_2CH_2CH_3$, $HOCH(CH_3)(CH_2CH_3)$, and $HOC(CH_3)_3$.

8. The indium oxo alkoxide of claim 1, wherein the indium oxo alkoxide is suitable for producing an indium oxide-containing coating.

9. The indium oxo alkoxide of claim 1, wherein the indium oxo alkoxide is suitable for producing a liquid coating composition.

10. The indium oxo alkoxide of claim 1, wherein the indium oxo alkoxide is suitable for producing an electronic component.

11. The indium oxo alkoxide of claim 10, wherein the electronic component is at least one selected from the group consisting of a transistor, a display, a RFID tag, a circuit, a diode, a sensor, and a solar cell.

12. The indium oxo alkoxide of claim 1, wherein X=Cl.

13. The indium oxo alkoxide of claim 1, wherein R is at least one selected from the group consisting of $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)(CH_2CH_3)$, and $-C(CH_3)_3$.

14. The indium oxo alkoxide of claim 1, wherein R is at least one selected from the group consisting of $-CH_2CH_2-OCH_3$, $-CH_2CH_2-OCH_2CH_3$, $-CH_2CH_2-OCH_2CH_2CH_3$, $-CH_2CH_2-OCH(CH_3)_2$, $-CH_2CH_2-OCH_2CH_2CH_2CH_3$, $-CH_2CH_2-OCH_2CH(CH_3)_2$, $-CH_2CH_2-OCH(CH_3)(CH_2CH_3)$, and $-CH_2CH_2-OC(CH_3)_3$.

15. The indium oxo alkoxide of claim 1, wherein R' is at least one selected from the group consisting of $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)(CH_2CH_3)$, and $-C(CH_3)_3$.

16. The indium oxo alkoxide of claim 1, wherein R" is at least one selected from the group consisting of $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)(CH_2CH_3)$, and $-C(CH_3)_3$.

17. The indium oxo alkoxide of claim 1, wherein R''' is at least one selected from the group consisting of $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)(CH_2CH_3)$, and $-C(CH_3)_3$.

18. The indium oxo alkoxide of claim 1, wherein x is of from 0 to 5 and y is of from 0 to 5.

19. The indium oxo alkoxide of claim 1, wherein x is of from 1 to 3, and y is of from 1 to 3.

20. The process of claim 3, wherein a molar ratio of the α-hydroxy ester R'CH(OH)COOR" to the indium(III) salt is greater than 0.33:1.

* * * * *